United States Patent [19]

Eckstein et al.

[11] 4,166,176
[45] Aug. 28, 1979

[54] FLUORESCENT DYESTUFFS

[75] Inventors: Udo Eckstein, Cologne; Horst Harnisch, Much, both of Fed. Rep. of Germany

[73] Assignee: Bayer Aktiengesellschaft, Leverkusen, Fed. Rep. of Germany

[21] Appl. No.: 888,237

[22] Filed: Mar. 20, 1978

[30] Foreign Application Priority Data

Mar. 23, 1977 [DE] Fed. Rep. of Germany ....... 2712686

[51] Int. Cl.² .................. C07D 403/10; C07D 413/10
[52] U.S. Cl. .................................... 542/460; 8/1 W; 252/301.23; 427/158; 542/434; 542/435; 542/454; 542/455; 542/456; 542/458
[58] Field of Search ............... 542/454, 455, 456, 458, 542/460, 434, 435; 252/301.23

[56] References Cited

U.S. PATENT DOCUMENTS

| | | | |
|---|---|---|---|
| 2,713,046 | 7/1955 | Williams et al. | 252/301.23 |
| 2,901,476 | 8/1959 | Gold et al. | 252/301.23 |
| 3,558,611 | 1/1971 | Fleck | 542/435 |
| 3,657,231 | 4/1972 | Booth | 542/435 |
| 3,732,221 | 5/1973 | Siegrist et al. | 542/460 |
| 3,757,010 | 9/1973 | Balzer et al. | 542/435 |
| 3,759,900 | 9/1973 | Horstmann | 542/461 |
| 3,808,202 | 4/1974 | Strobel | 542/460 |
| 3,817,991 | 6/1974 | Meyer et al. | 542/460 |
| 3,951,965 | 4/1976 | Mengler et al. | 542/434 |
| 4,032,558 | 6/1977 | Fleck et al. | 542/460 |

*Primary Examiner*—Arthur P. Demers
*Attorney, Agent, or Firm*—Plumley & Tyner

[57] ABSTRACT

The compounds of the formula

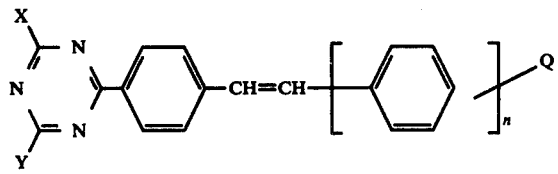

wherein
X and Y denote halogen, hydroxyl, amino, alkoxy, aralkyloxy, cycloalkoxy, aryloxy, alkylmercapto, arylmercapto, alkylamino, dialkylamino, morpholino, piperidino, piperazino, pyrrolidino, acylamino, arylamino or alkyl,
n denotes 0, 1 or 2 and
Q denotes hydrogen, pyrazol-1-yl, oxazol-2-yl, benzoxazol-2-yl, naphthoxazol-2-yl, 1,2,4-oxadiazol-5-yl, 1,3,4-oxadiazol-2-yl, isoxazol-3-yl, isoxazol-5-yl, thiazol-2-yl, benzthiazol-2-yl, 1,3,4-thiadiazol-2-yl, imidazol-2-yl, benzimidazol-2-yl, 1,2,3-triazol-2-yl, 1,2,3-triazol-4-yl, 1,2,4-triazol-3-yl, 1,2,4-triazol-5-yl, 2 H-benzotriazol-2-yl, 2 H-naphthotriazol-2-yl, benzo[b]-furan-2-yl, naphtho[2,1-b]-furan-2-yl, benzo[b]-thiophen-2-yl, naphtho[2,1-b]-thiophen-2-yl, pyrimidin-2-yl, pyrridin-2-yl, quinazolin-4-yl or quinazolin-2-yl, if n is 1 or 2, or denotes naphthyl-, stilben-4-yl-, benzo[b]-furan-6-yl, dibenzofuran-3-yl-, dibenzofuran-2-yl, quinoxalin-6-yl-, quinazolin-6-yl- or 2 H-benzotriazol-5-yl, if n is 0, it being possible for the cyclic and non-cyclic radicals to carry the non-chromophoric substituents customary for whiteners are suitable for whitening organic materials.

6 Claims, No Drawings

FLUORESCENT DYESTUFFS

The invention relates to fluorescent dyestuffs, processes for their preparation and their use for whitening organic materials.

The new compounds correspond to the formula

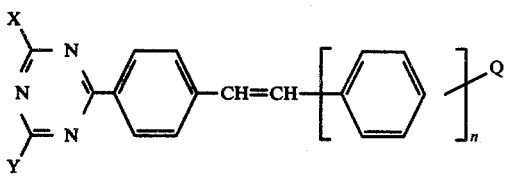

wherein
- X and Y denote halogen, hydroxyl, amino, alkoxy, aralkyloxy, cycloalkoxy, aryloxy, alkylmercapto, arylmercapto, alkylamino, dialkylamino, morpholino, piperidino, piperazino, pyrrolidino, acylamino, arylamino or alkyl,
- n denotes 0, 1 or 2 and
- Q denotes hydrogen, pyrazol-1-yl, oxazol-2-yl, benzoxazol-2-yl, naphthoxazol-2-yl, 1,2,4-oxadiazol-5-yl, 1,3,4-oxadiazol-2-yl, isoxazol-3-yl, isoxazol-5-yl, thiazol-2-yl, benzthiazol-2-yl, 1,3,4-thiadiazol-2-yl, imidazol-2-yl, benzimidazol-2-yl, 1,2,3-triazol-2-yl, 1,2,3-triazol-4-yl, 1,2,4-triazol-3-yl, 1,2,4-triazol-5-yl, 2H-benzotriazol-2-yl, 2H-naphtho-triazol-2-yl, benzo[b]-furan-2-yl, naphtho[2,1-b]-furan-2-yl, benzo[b]-thiophen-2-yl, naphtho[2,1-b]-thiophen-2-yl, pyrimidin-2-yl, pyrridin-2-yl, quinazolin-4-yl or quinazolin-2-yl, if n is 1 or 2, or denotes naphthyl-, stilben-4-yl-, benzo[b]-furan-6-yl, dibenzofuran-3-yl-, dibenzofuran-2-yl, quinoxalin-6-yl-, quinazolin-6-yl- or 2H-benzotriazol-5-yl, if n is 0, it being possible for the cyclic and non-cyclic radicals to carry the non-chromophoric substituents customary for whiteners.

n is preferably 1.

Non-chromophoric substituents are, for example, halogen, optionally substituted alkyl, optionally substituted alkenyl, aryl, aralkyl, optionally substituted alkoxy, alkoxycarbonyl, optionally substituted aminocarbonyl, cyano, alkylsulphonyl, alkoxysulphonyl, optionally substituted aminosulphonyl, acyl, acylamino, hydroxyl, aryloxy, aralkyloxy, alkenyloxy, aryloxycarbonyl, aralkyloxycarbonyl, carboxyl or acyloxy.

Alkyl is, in particular, $C_1$–$C_4$-alkyl, which can be monosubstituted by hydroxyl, $C_1$–$C_4$-alkoxy, cyano, carboxyl, $C_1$–$C_4$-alkoxycarbonyl, aminocarbonyl, chlorine or bromine, or is trifluoromethyl.

Alkenyl is, in particular, $C_2$–$C_5$-alkenyl, which can be monosubstituted by hydroxyl, $C_1$–$C_4$-alkoxy, cyano, carboxyl, $C_1$–$C_4$-alkoxycarbonyl, chlorine or bromine.

Halogen is, in particular, fluorine, chlorine and bromine, preferably chlorine. Aryl is, in particular, phenyl which is optionally substituted by $C_1$–$C_4$-alkyl, trifluoromethyl, chlorine, bromine or $C_1$–$C_4$-alkoxy.

Aralkyl is, in particular, phenyl-$C_1$–$C_4$-alkyl, which can also be substituted in the phenyl nucleus by chlorine, methyl or methoxy.

Alkoxy is, in particular, $C_1$–$C_4$-alkoxy, or a radical of the formula

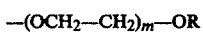
—(OCH$_2$—CH$_2$)$_m$—OR wherein
- R denotes hydrogen or $C_1$–$C_4$-alkyl and
- m denotes an integer from 1 to 20.

Cycloalkyloxy is, in particular, cyclopentyloxy and cyclohexyloxy.

Acyl is, in particular, $C_1$–$C_4$-alkylcarbonyl, $C_1$–$C_4$-alkylsulphonyl, benzoyl which is optionally substituted by methyl, methoxy or chlorine or benzenesulphonyl which is optionally substituted by methyl, methoxy or chlorine.

Possible substituents of the aminocarbonyl and aminosulphonyl radicals are, in particular, $C_1$–$C_4$-alkyl, phenyl which is optionally substituted by methyl, methoxy or chlorine or phenyl-$C_1$–$C_4$-alkyl.

Preferred compounds correspond to the formula

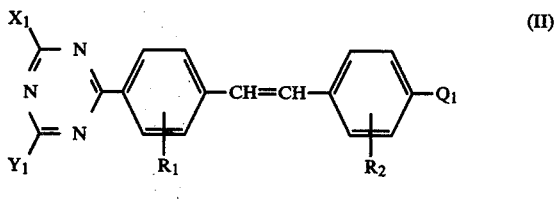

wherein
- $X_1$ and $Y_1$ denote chlorine, $C_1$–$C_4$-alkylamino, di-$C_1$–$C_4$-alkylamino, morpholino, piperidino, phenylamino or a radical of the formula

—(OCH$_2$—CH$_2$)$_q$—OR$_3$ $R_1$ and $R_2$ denote hydrogen, chlorine, $C_1$–$C_4$-alkyl, $C_1$–$C_4$-alkoxy, $C_1$–$C_4$-alkoxycarbonyl or cyano, $R_3$ denotes hydrogen, $C_1$–$C_4$-alkyl, benzyl or phenyl, $Q_1$ denotes chlorine, bromine, cyano, carboxyl, $C_1$–$C_4$-alkoxycarbonyl or a radical of the formulae

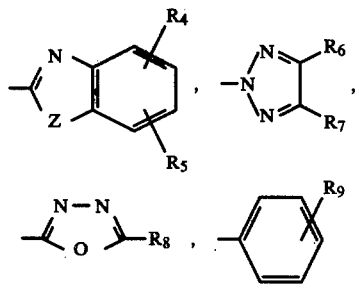

$R_4$ denotes hydrogen, chlorine, $C_1$–$C_4$-alkyl, phenyl-$C_1$–$C_3$-alkyl, cyclohexyl, phenyl, $C_1$–$C_4$-alkoxy, $C_1$–$C_4$-alkylsulphonyl, $C_1$–$C_4$-alkoxycarbonyl, cyano or carboxyl or, together with $R_5$, a fused 1-cyclopentene, 1-cyclohexene or benzene ring which is optionally substituted by 1 to 4 methyl groups, $R_5$ denotes hydrogen, chlorine or methyl or, together with $R_4$, a fused 1-cyclopentene, 1-cyclohexene or benzene ring which is optionally substituted by 1 to 4 methyl groups, $R_6$ denotes $C_1$–$C_4$-alkyl, phenyl or styryl or, together with $R_7$, a fused benzene ring which is optionally substituted by $C_1$–$C_4$-alkyl, $C_1$–$C_4$-alkoxy or chlorine or a fused naphthalene ring, $R_7$ denotes hydrogen, $C_1$–$C_4$-alkyl or phenyl or, together with $R_6$, a fused benzene ring which is optionally substituted by $C_1$–$C_4$-alkyl, $C_1$–$C_4$-alkoxy or chlorine or a fused naphthalene ring, $R_8$ denotes phenyl, styryl, biphenylyl or naphthyl which are optionally substituted by $C_1$-$C_4$-alkyl, $C_1$-$C_4$-alkoxy, $C_1$-$C_4$-alkoxycarbonyl, cyano or chlorine, $R_9$ denotes hydrogen, $C_1$-$C_4$-alkyl, $C_1$-$C_4$-alkoxy, $C_1$-$C_4$-alkoxycarbonyl, cyano or a benzoxazol-2-yl radical which is optionally substituted by $C_1$-$C_4$-alkoxycarbonyl, cyano or chlorine, Z denotes O, S or $NR_{10}$, $R_{10}$ denotes hydrogen, $C_1$-$C_4$-alkyl, acetyl, benzoyl, benzyl or phenyl and q denotes an integer from 0 to 7.

Particularly valuable compounds of the formula (II) are those in which $X_1$ and $Y_1$ denote $-(OCH_2-CH_2)_r-OR_{11}$, $Q_1$ denotes a radical of the formulae

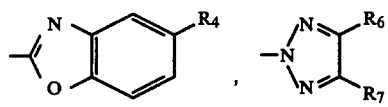

r denotes an integer from 0 to 2, $R_1$ and $R_2$ denote hydrogen or cyano, $R_4$ denotes hydrogen, chlorine, $C_1$-$C_4$-alkyl, phenyl-$C_1$-$C_3$-alkyl, cyclohexyl, phenyl, $C_1$-$C_4$-alkoxy, $C_1$-$C_4$-alkylsulphonyl, $C_1$-$C_4$-alkoxycarbonyl, cyano or carboxyl, $R_{11}$ denotes $C_1$-$C_4$-alkyl and $R_6$ and $R_7$ have the abovementioned meaning.

The fluorescent dyestuffs according to the invention can be prepared in various ways. Preferably, (a) a phosphono compound of the formula

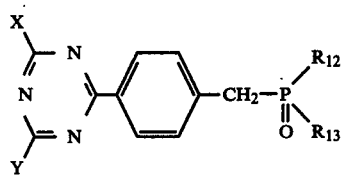

(III)

wherein

X and Y have the abovementioned meaning and the benzene ring can contain further non-chromophoric substituents and $R_{12}+R_{13}$ denote $C_1$-$C_4$-alkoxy, $C_5$-$C_6$-cycloalkoxy or phenoxy, is subjected to a condensation reaction with an aldehyde of the formula

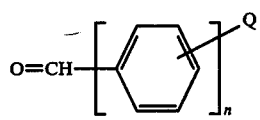

(IV)

wherein

Q and n have the abovementioned meaning and the benzene ring can contain further non-chromophoric substituents, or (b) a phosphono compound of the formula

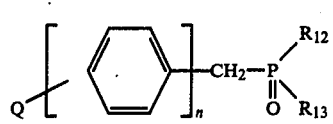

(V)

wherein

Q, $R_{12}$, $R_{13}+n$ have the abovementioned meaning and the benzene ring can be substituted by non-chromophoric substituents, is subjected to a condensation reaction with an aldehyde of the formula

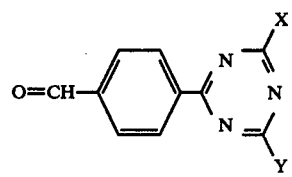

(VI)

wherein

X and Y have the abovementioned meaning and the benzene ring can be substituted by non-chromophoric substituents, in organic solvents in the presence of basic condensing agents.

The solvents chosen are advantageously inert solvents, for example hydrocarbons, such as toluene or xylene, or alcohols, such as methanol, ethanol, isopropanol, butanol, glycol, glycol ethers, such as 2-methoxyethanol, hexanol, cyclohexanol or cyclooctanol, furthermore ethers, such as diisopropyl ether, dioxane or tetrahydrofurane, and also formamides or N-methylpyrrolidone. Bipolar organic solvents, such as dimethylformamide and dimethylsulphoxide, are particularly suitable.

Condensing agents which can be used are strongly basic compounds, such as alkali metal hydroxides and alkaline earth metal hydroxides, alkali metal amides and alkaline earth metal amides and alkali metal alcoholates and alkaline earth metal alcoholates, for example potassium hydroxide, sodium hydroxide, potassium tert.-butylate, sodium amide or sodium methylate, furthermore alkali metal compounds of dimethylsulphoxide and alkali metal hydrides, and optionally alkali metal dispersions.

The reaction is preferably carried out in a temperature range from 0° to 100° C. The compounds according to the invention are also obtained if, instead of the phosphono compounds III and V, the corresponding quaternary phosphonium salts, for example the triphenylphosphonium salts, are used and these are subjected to a condensation reaction with the aldehydes IV and VI respectively, via the phosphorylene stage.

It is also possible, of course, to carry out further conversions, which are in themselves known, on the reaction products of the above processes, such as halogenation reactions, functional modifications of carboxyl groups, introduction of chloromethyl groups or replacement of halogen atoms by cyano groups.

Because of their absorption in the ultraviolet region and their fluorescence, the compounds according to the invention are suitable for whitening the most diverse synthetic, semi-synthetic and natural organic high-molecular materials, such as are indicated in detail in the following.

I. Synthetic organic high-molecular materials:

(a) Polymerisation products based on organic compounds containing at least one polymerisable carbon-carbon double bond, that is to say their homopolymers or copolymers as well as their after-treatment products, such as, for example, crosslinking, grafting or degradation products, polymer blends and the like, of which the following may be mentioned as examples: polymers based on α,β-unsaturated carboxylic acids, especially on acrylic compounds (such as, for example, acrylic esters, acrylic acids, acrylonitrile, acrylamides and their derivatives or their methacrylic analogues), and on olefine hydrocarbons (such as, for example, ethylene, propylene, isobutylene, styrenes and dienes, such as, in particular, butadiene and isoprene, that is to say, also rubbers and rubber-like polymers, and also so-called ABS polymers), polymers based on vinyl and vinylidene compounds (such as, for example, vinyl esters, vinyl chloride, vinylsulphonic acid, vinyl ether, vinyl alcohol, vinylidene chloride and vinylcarbazole), on halogenated hydrocarbons (chloroprene and post-halogenated ethylenes), on unsaturated aldehydes and ketones (for example acrolein and the like) and on allyl compounds and the like, graft polymerisation products (for example those obtained by the grafting on of vinyl monomers), crosslinked products (for example those obtained by means of bifunctional or polyfunctional crosslinking agents, such as divinylbenzene, polyfunctional allyl compounds or bisacrylic compounds) or are obtainable by partial degradation (hydrolysis or depolymerisation) or modification of reactive groupings (for example esterification, etherification, halogenation or spontaneous crosslinking).

(b) Other polymerisation products, such as are obtainable, for example, by ring opening, for example polyamides of the polycaprolactam type, and also formaldehyde polymers or polymers which are obtainable both via polyaddition and via polycondensation, such as polyethers, polythioethers, polyacetals or thioplasts.

(c) Polycondensation products or precondensates based on bifunctional or polyfunctional compounds having condensable groups, their homocondensation and co-condensation products as well as after-treatment products, of which the following may be mentioned as examples: polyesters, that is to say polyesters which are saturated (for example polyethylene terephthalate) or unsaturated (for example maleic acid/dialcohol polycondensates as well as their crosslinking products with copolymerisable vinyl monomers), unbranched or branched (also those based on polyhydric alcohols, such as, for example, alkyd resins); and polyamides (for example hexamethylenediamine adipate), maleate resins, melamine resins, phenolic resins, aniline resins, furane resins, carbamide resins and also their precondensates and products of analogous structure, polycarbonates, silicone resins and others.

(d) Polyaddition products, such as polyurethanes (crosslinked and non-crosslinked) and epoxide resins.

II. Semi-synthetic organic materials, such as, for example, cellulose esters or mixed esters (acetate or propionate), nitrocellulose, cellulose ethers, regenerated cellulose (viscose or copper ammonium cellulose), or their after-treatment products, and casein plastics.

III. Natural organic materials of animal or vegetable origin, for example based on cellulose or proteins, such as wool, cotton, silk, bast, jute, hemp, skins and hairs, leather, finely divided wood compositions, natural resins (such as colophonium and in particular lacquer resins), and also rubber, guttapercha and balata, as well as their after-treatment and modification products (for example those obtained by curing, crosslinking or grafting), degradation products (for example those obtained by hydrolysis or depolymerisation) and those products obtainable by modifying reactive groups (for example by acylation, halogenation, crosslinking and the like).

The organic materials which can be used can be in the most diverse states of processing (raw materials, semi-finished goods or finished goods) and states of aggregation. On the one hand, they can be in the form of structures of the most diverse shapes, that is to say, for example, predominantly three-dimensional bodies, such as blocks, slabs, profiles, tubes, injection mouldings or the most diverse machined articles, chips or granules or foams; predominantly two-dimensional bodies, such as films, sheets, lacquers, tapes, coverings, impregnations and coatings, or predominantly one-dimensional bodies, such as filaments, fibres, flocks, bristles and wires. The said materials can, on the other hand, also be in un-shaped states in the most diverse homogeneous and inhomogeneous forms of division and states of aggregation, for example in the form of powders, solutions, emulsions, dispersions and latices (examples: lacquer solutions, polymer dispersions, sols, jellies, putties, pastes, waxes, adhesive compositions and trowelling compounds, and the like).

Fibre materials can, for example, be in the form of continuous filaments, staple fibres, flocks, hanks, textile filaments, yarns, threads, fibre fleeces, felts, waddings, flocked structures or woven textile fabrics or textile laminates, knitted fabrics and paper, cardboards or paper pulps and the like.

The compounds to be used according to the invention are also of importance for the treatment of organic textile materials, especially woven textile fabrics. Where fibres, which can be in the form of staple fibres or continuous fibres or in the form of hanks, woven fabrics, knitted fabrics, fleeces, flocked substrates or laminates, are to be whitened according to the invention, this is advantageously effected in an aqueous medium, in which the compounds concerned are present in a finely divided form (suspension or, in some cases, solution). If appropriate, dispersing agents can be added during the treatment, such as, for example, soaps, polyglycol ethers of fatty alcohols, fatty amines or alkylphenols, cellulose sulphite waste liquors or condensation products of optionally alkylated naphthalenesulphonic acids and formaldehyde. It proves particularly advantageous to carry out the treatment in a neutral, weakly alkaline or acid bath. It is also advantageous to carry out the treatment at elevated temperatures of about 50° to 100° C., for example at the boiling point of the bath or near it (about 90° C.). Solutions in organic solvents can also be used for the finishing according to the invention, as is practised in the dyeing trade in so-called solvent dyeing (pad-thermofix application or the exhaustion dyeing process in drum dyeing machines), for example for polyamide and polyester substrates.

The new whiteners to be used according to the invention can furthermore be added to, or incorporated in, the materials before or during their shaping. Thus, for example in the production of films, sheets, tapes or shaped articles, they can be added to the compression moulding composition or injection moulding composition, or they can be dissolved or dispersed, or otherwise homogeneously finely distributed, in the spinning compositions before spinning. The whiteners can also be added to the starting materials, reaction mixtures or intermediate products for the preparation of fully synthetic or semi-synthetic organic materials, that is to say also before or during the chemical reaction, for example in the case of a polycondensation reaction (that is to say also to the precondensates), in the case of a polymerisation reaction (that is to say also to the prepolymers) or of a polyaddition reaction.

The new whiteners can, of course, also be employed in all cases where organic materials of the type indicated above are combined with inorganic materials in any form (typical examples: washing agents or white pigments in organic substances).

The new whitening substances are distinguished by a particularly good resistance to heat, fastness to light and resistance to migration.

The amount of new whiteners to be used according to the invention, relative to the material to be whitened, can vary within wide limits. A distinct and durable effect is achieved even with very small amounts, in certain cases, for example, amounts of 0.001% by weight. However, amounts of up to about 0.5% by weight and more can be used. For most practical purposes, amounts between 0.01 and 0.2% by weight are of preferred interest.

The new compounds which are used as whiteners can also be employed, for example, as follows:

(a) Mixed with dyestuffs or pigments or as an additive to dye-baths, printing pastes, discharge pastes or reserve pastes. Furthermore, also, for the after-treatment of dyeings, prints or discharge prints.

(b) Mixed with so-called "carriers", antioxidants, light stabilisers, heat stabilisers and chemical bleaching agents or as an additive to bleaching baths.

(c) Mixed with crosslinking agents or finishing agents, such as starch or synthetically accessible finishes. The products according to the invention can also advantageously be added to the liquors used for achieving a creaseproof finish.

(d) In combination with washing agents. The washing agent and brightener can be added separately to the wash baths which are to be used. It is also advantageous to use washing agents which contain the whiteners as an admixture. Suitable washing agents are, for example, soaps, salts of sulphonate washing agents, such as, for example, of sulphonated benzimidazoles which are substituted on the 2-carbon atom by higher alkyl radicals, and also salts of monocarboxylic acid esters of 4-sulphophthalic acid with higher fatty alcohols, and furthermore salts of fatty alcohol sulphonates, alkylarylsulphonic acids or condensation products of higher fatty acids with aliphatic hydroxysulphonic or aminosulphonic acids. Nonionic washing agents can also be used, for example polyglycol ethers which are derived from ethylene oxide and higher fatty alcohols, alkylphenols or fatty amines.

(e) In combination with polymeric carriers (polymerisation, polycondensation or polyaddition products), in which the whiteners are incorporated, optionally in addition to other substances, in the dissolved or dispersed form, for example in the case of coating agents, impregnating agents or binding agents (solutions, dispersions, emulsions), textiles, fleeces, paper or leather.

(f) As additives to the most diverse industrial products, in order to render these more marketable or to avoid disadvantages in their applicability, for example as an additive to sizes, adhesives, toothpastes, paints and the like.

(g) In combination with other substances having a whitening action (for example for the purpose of altering the shade).

(h) In spinning bath formulations, that is to say as additives to spinning baths, such as are used for improving the slip for the further processing of synthetic fibres.

The compounds of the formula initially indicated can be used as scintillators for various purposes of a photographic nature, such as for electrophotographic reproduction or for supersensitisation.

If the whitening process is combined with other treatment or finishing methods, the combined treatment is advantageously carried out with the aid of corresponding stable formulations. Such formulations are characterised in that they contain the whitening compounds of the general formula initially indicated, as well as dispersing agents, washing agents, carriers, dyestuffs, pigments or finishing agents.

In the treatment of a range of fibre substrates, for example polyester fibres, using the whiteners according to the invention, the procedure followed is appropriately to impregnate these fibres with the aqueous dispersions of the whiteners at temperatures below 75° C., for example at room temperature, and to subject them to a dry heat treatment at temperatures above 100° C., it being generally advisable additionally to dry the fibre material beforehand at a moderately elevated temperature, for example at not less than 60° C. up to about 100° C. The heat treatment in the dry state is then advantageously carried out at temperatures between 120° and 225° C., for example by warming in a drying chamber, by ironing in the temperature range indicated or also by treatment with dry, superheated steam. The drying and dry heat treatment can also be carried out in immediate succession or can be combined in a single operation.

EXAMPLE 1

12 g (0.22 mol) of sodium methylate are added in portions to a solution of 33.9 g (0.1 mol) of 2,4-dimethoxy-6-(4-dimethoxyphosphonomethylphenyl)-1,3,5-triazine and 18.2 g (0.1 mol) of 4-formylbiphenyl in 200 ml of dimethylformamide in the course of 15 minutes. The reaction mixture is stirred at 50° C. for 5 hours, discharged on to 1 l of ice-water and adjusted to pH 3 to 4 with concentrated hydrochloric acid. This gives 29.5 g (75% of theory) of crude product of the formula

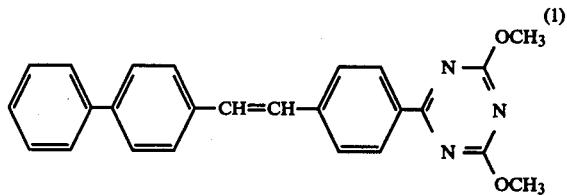

Recrystallisation from dimethylformamide and from chlorobenzene gives light yellow crystals which, when dissolved in dimethylformamide, give a solution which exhibits deep blue fluorescence and which exhibits a powerful brightening effect when incorporated into polyester.

The dimethoxyphosphonomethyl compound used of the formula

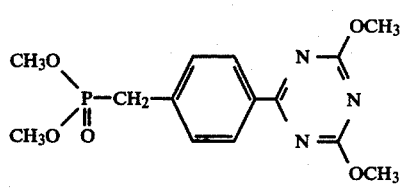

is prepared in the following manner:

A mixture of 18.2 g (0.1 mol) of N-bromosuccinimide and 0.2 g of azoisobutyronitrile is added in portions to a solution of 23.1 g (0.1 mol) of 2,4-dimethoxy-6-(4-methylphenyl)-1,3,5-triazine and 0.1 g of dibenzoyl peroxide in 200 ml of anhydrous carbon tetrachloride at 60° C. in the course of 20 minutes, and the mixture is stirred for 4 hours at the reflux temperature. Thereafter, the succinimide is filtered off at 60° C., the filter cake is rinsed with hot carbon tetrachloride (about 50 to 100 ml) and the filtrate is evaporated almost to dryness. The residue is filtered off and washed with petroleum ether (40° to 80° C.). This gives 27.6 g (89% of theory) of the bromomethyl compound of melting point 146° C.; colourless crystals of melting point 154° C. from ethyl acetate.

31 g (0.1 mol) of crude 2,4-dimethoxy-6-(4-bromomethylphenyl)-1,3,5-triazine are warmed slowly to 140° C. with 75 g of trimethyl phosphite, whilst stirring, and the mixture is then stirred at this temperature for 4 hours. Most of the excess trimethyl phosphite is then distilled off in vacuo and 100 ml of cyclohexane are added to the residue. The mixture is cooled to 0° C. and allowed to crystallise out. Yield: 33 g (97.3% of theory) of colourless crystals of melting point 103° C.; colourless crystals of melting point 107° C. from methylcyclohexane.

EXAMPLE 2

34 g (0.11 mol) of 2,4-dimethoxy-6-(4-bromomethylphenyl)-1,3,5-triazine, 56 g of triethyl phosphite and 100 ml of dimethylformamide are heated to 120° to 150° C. for 4 hours. Thereafter, the excess triethyl phosphite and most of the dimethylformamide are distilled off in vacuo. The residue is dissolved in 250 ml of dimethylformamide with 14.4 g (0.1 mol) of 4-cyanobenzaldehyde, and 12 g (0.22 mol) of sodium methylate are added in portions. The reaction mixture is stirred for 3 hours at 50° C. and then discharged onto 1 l of ice-water and neutralised with acetic acid. The precipitate is filtered off, washed and then recrystallised from dimethylformamide/active charcoal. Yield: 22 g (64% of theory) of the compound of the formula

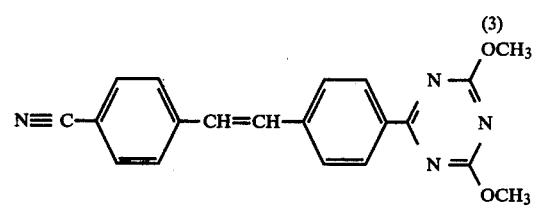

Fluorescence in dimethylformamide: blue.

The compounds of the general formula

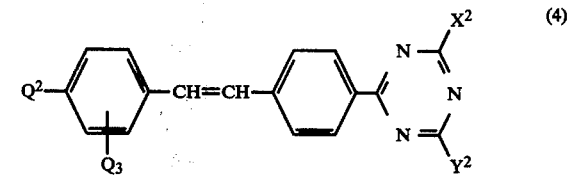

listed in Table I can be prepared likewise.

Table I

| Formula No. | $Q_2$ | $Q_3$ | $X_2$ | $Y_2$ | Colour of fluorescence in dimethylformamide |
| --- | --- | --- | --- | --- | --- |
| 5 | Cyano | 2-Cyano | Methoxy | Methoxy | blue |
| 6 | Carboxyl | 2-Chloro | Methoxy | Morpholino | red-violet |
| 7 | Ethoxycarbonyl | Ethoxycarbonyl | 2-Methoxy-ethoxy | 2-Methoxy-ethoxy | blue |
| 8 | Cyano | 3-Cyano | Dimethylamino | Dimethylamino | blue |
| 9 | Cyano | Methoxy | Morpholino | Morpholino | greenish-tinged blue |
| 10 | Cyano | H | Dibutylamino | Dibutylamino | greenish-tinged blue |
| 11 | Cyano | 2-Cyano | $(OC_2H_4)_2OCH_3$ | $(OC_2H_4)_2OCH_3$ | reddish-tinged blue |
| 12 | p-Cyanoanilino | H | tert.-Butoxy | tert.-Butoxy | blue |
| 13 | Cyano | 3-Butyl | $(OC_2H_4)_2OH$ | $(OC_2H_4)_2OH$ | blue |
| 14 | Methylsulphonyl | 3-Butoxy | 2-Hydroxyethylamino | 2-Hydroxyethylamino | blue |

EXAMPLE 3

12 g (0.22 mol) of sodium methylate are added in portions to a suspension of 31.7 g (0.1 mol) of 2-(4-dimethoxyphosphonomethyl-phenyl)benzoxazole and 24.5 g (0.1 mol) of 2,4-dimethoxy-6-(4-formylphenyl)-1,3,5-triazine in 300 ml of dimethylformamide in the course of 20 minutes. The reaction mixture is stirred at 40° to 50° C. for 3 hours and then discharged onto 1 l of ice-water and adjusted to pH 5 to 7 with concentrated hydrochloric acid. The yellowish precipitate is filtered off, washed with water and dried. This gives 42 g (96% of theory) of crude product of the formula

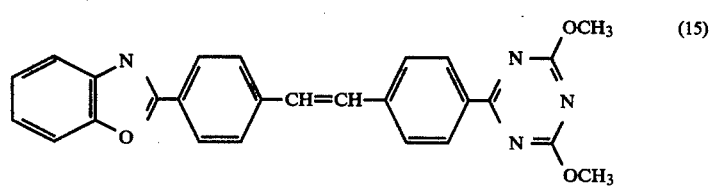

which is purified by recrystallising several times from 1,2-dichlorobenzene. When the substance is dissolved in dimethylformamide, the solution exhibits deep blue fluorescence, and the substance has a powerful brightening effect with good fastness properties when incorporated into polyester.

The aldehyde used, of the formula

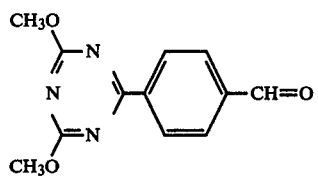
(16)

is prepared in the following manner:

31 g (0.1 mol) of crude 2,4-dimethoxy-6-(4-bromomethyl-phenyl)-1,3,5-triazine (prepared according to Example 1) are boiled under reflux with 15.5 g (0.11 mol) of hexamethylenetetramine in 100 ml of chloroform for 4 hours. Thereafter, 50 ml of chloroform are distilled off, the mixture is cooled and 50 ml of acetone are added. After filtering, 40.2 g of the urotropine salt are obtained and are heated under reflux in 100 ml of 50% strength acetic acid for 2 hours. The solution is adjusted to pH 3 with about 10 to 20 ml of concentrated hydrochloric acid and, after boiling for a short time, is cooled to 0° C. and 500 ml of water are added. The precipitate which has separated out is filtered off and washed with water until neutral. This gives 15 g (61.2% of theory) of colourless crystals of melting point 136°–138° C.; colourless needles of melting point 149°–150° C. from methylglycol.

The aldehyde of the formula

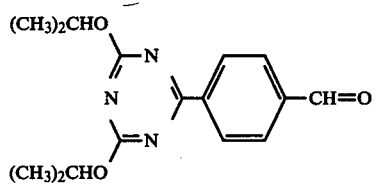
(17)

is also prepared analogously, yield: 72% of theory, melting point: 109° C.

2-(4-Dimethoxyphosphonomethyl-phenyl)-benzoxazole was prepared in a known manner by brominating 2-tolylbenzoxazole and subsequently reacting the bromination product with trimethyl phosphite.

EXAMPLE 4

Analogously to Example 3, the reaction of (17) with 2-(4-dimethoxyphosphonomethyl-phenyl)-benzoxazole gives 40 g (81% of theory) of the compound of the formula

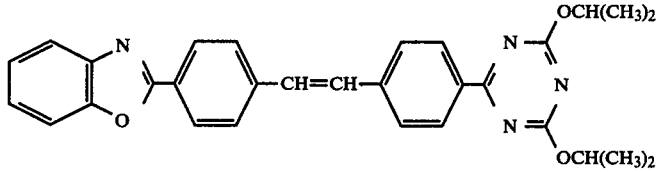
(18)

in the form of yellow crystals. They can be purified by recrystallising from xylene, with the addition of bleaching earth; fluorescence in dimethylformamide: reddish-tinged blue.

EXAMPLE 5

In the same way as in Example 3, 25.7 g (0.1 mol) of 5-chloro-2-(4-formylphenyl)benzoxazole and 33.9 g (0.1 mol) of 2,4-dimethoxy-6-(4-dimethoxyphosphonomethyl-phenyl)-1,3,5-triazine give 36.5 g (78% of theory) of the compound of the formula

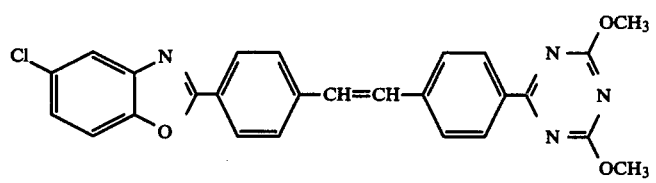
(19)

Recrystallisation from chlorobenzene gives pale yellow crystals which, when dissolved in dimethylformamide, give a solution which exhibits intensive reddish-tinged blue fluorescence.

EXAMPLE 6

34.6 g (0.1 mol) of 5-carbomethoxy-2-(4-bromomethylphenyl)-benzoxazole (prepared from 5-carbomethoxy-2-(4-methylphenyl)-benzoxazole with the aid of N-bromosuccinimide), 75 g (0.6 mol) of trimethyl phosphite and 200 ml of dimethylformamide are warmed to 120° C., whilst stirring, and further heated to 140° C. in the course of 4 hours. Trimethyl phosphite and most of the dimethylformamide are then distilled off in vacuo. The residue is dissolved in 200 ml of dimethylformamide with 24.5 g (0.1 mol) of 2,4-dimethoxy-6-(4-formylphenyl)-1,3,5-triazine-2, and 12 g (0.22 mol) of sodium methylate are added in portions. After the suspension has been stirred at 50° C. for 3 hours, the reaction mixture is discharged onto 500 ml of water, and 100 ml of acetic acid are added. Cooling the mixture to 0° C. and filtering off the precipitate and washing it with water gives 45 g (91% of theory) of the compound of the formula

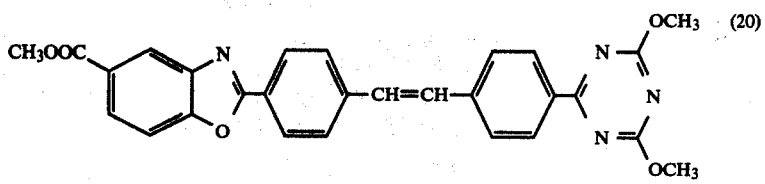

in the form of a light yellow crystalline powder, which is purified by recrystallisation from chlorobenzene; fluorescence in dimethylformamide: reddish-tinged blue.

The saponification of the methyl ester gives the free carboxylic acid of the formula

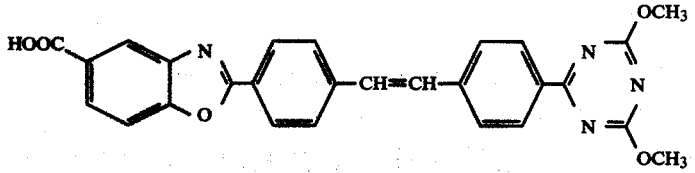

The saponification was carried out by boiling the methyl ester with aqueous, ethanolic sodium hydroxide solution.

EXAMPLE 7

40.2 g (0.11 mol) of 2-N-morpholino-4-methoxy-6-(4-bromomethyl-phenyl)-1,3,5-triazine, 56 g of triethyl phosphite and 100 ml of dimethylformamide are stirred at 120° to 150° C. for 4 hours. Thereafter, the excess triethyl phosphite and most of the dimethylformamide are distilled off in vacuo. The residue is suspended in 200 ml of dimethylformamide with 15 g (0.11 mol) of 4-formylbenzoic acid. 12.6 g of 30% strength sodium methylate solution are added dropwise to this suspension in the course of 20 minutes and the reaction mixture is stirred at 50° C. for 3 hours.

Thereafter, the mixture is cooled, discharged onto 500 ml of water and adjusted to pH 2 to 3 with concentrated hydrochloric acid. Filtering off the precipitate and washing it with water gives 33.5 g (80% of theory) of light yellow crystals of melting point 295°–297° C. of the formula

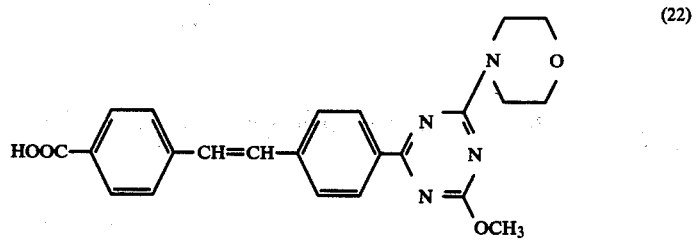

which are purified by recrystallising from dimethylformamide.

41.9 g (0.1 mol) of the crude product of the compound (22) described above are converted into the acid chloride with 15 g (0.12 mol) of thionyl chloride and 2 g of dimethylformamide in 100 ml of anhydrous xylene (reflux for about 2 hours). A mixture of 12.4 g (0.1 mol) of 3-amino-4-hydroxytoluene and 13 g (0.11 mol) of N,N-dimethylaniline in 80 ml of dioxane is then added dropwise at room temperature, under nitrogen. After warming the reaction mixture to 80° C. for five hours, it is freed from xylene with steam. The product which has separated out is filtered off, washed with dilute hydrochloric acid and water and, after drying in vacuo, is heated under nitrogen with 0.5 g of boric acid in a mixture of 50 ml of distilled chlorobenzene and 150 ml of trichlorobenzene to 160° C. for 3 hours and then to 205° to 210° C. for 1 hour, about 120 to 150 ml of solvent being distilled off azeotropically with the water formed. After cooling, the residue is allowed to crystallise, with the addition of 80 ml of methanol; yield: 36.4 g (72% of theory) of the compound of the formula

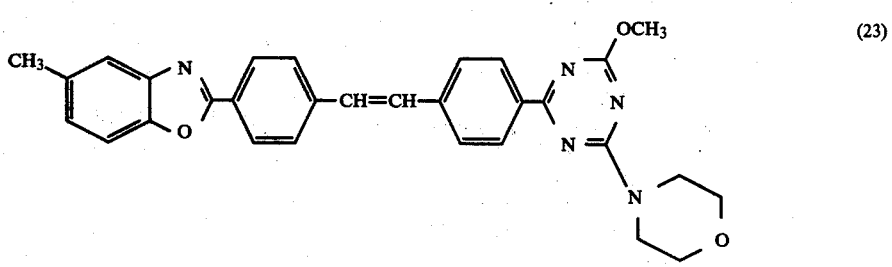

Recrystallisation from 1,2-dichlorobenzene, with the addition of bleaching earth, gives yellow crystals which, when dissolved in dimethylformamide, give a solution which exhibits deep blue fluorescence.

EXAMPLE 8

If the procedure followed is according to Example 7, but 4-amino-5-hydroxy-1,2-xylene is used instead of 3-amino-4-hydroxytoluene, the compound of the formula

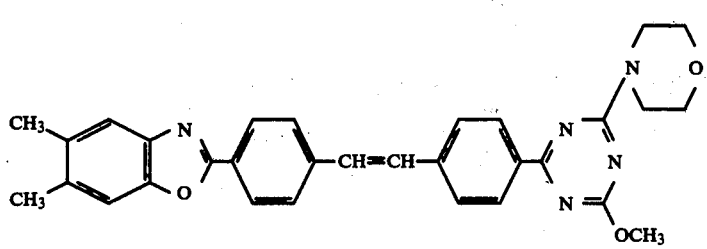

is obtained in the form of light yellow crystals in 80% yield. The substance exhibits blue fluorescence in dimethylformamide.

The stilbene derivatives of the general formula

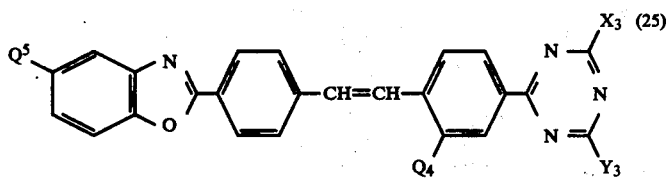

listed in Table II are prepared according to Example 3 or 7.

EXAMPLE 9

Replacing 2-(4-dimethoxyphosphonomethyl-phenyl)-benzoxazole in Example 3 by the equivalent amount of 2-(4-dimethoxyphosphonomethyl-phenyl)-naphth[1,2-d]-oxazole gives the compound of the formula

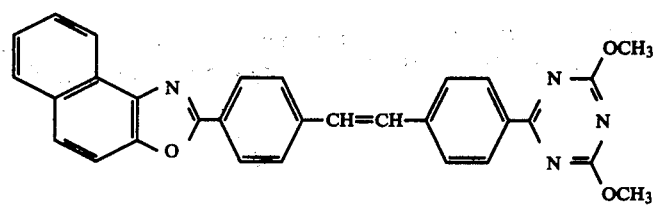

in 80% yield in the form of light yellow crystals which, when recrystallised from dimethylformamide, exhibit blue fluorescence in dimethylformamide.

EXAMPLE 10

34 g (0.11 mol) of 2,4-dimethoxy-6-(4-bromomethyl-phenyl)-1,3,5-triazine are reacted with 24.9 g (0.1 mol) of 2-(4-formylphenyl)-4-phenyl-2H-1,2,3-triazole via the dimethoxyphosphonomethyl compound, according to Example 2. This gives the compound of the formula Table II

| Formula No. | $Q_4$ | $Q_5$ | $X_3$ | $Y_3$ | Colour of fluorescence in dimethylformamide |
| --- | --- | --- | --- | --- | --- |
| 26 | H | H | Chlorine | Chlorine | deep blue |
| 27 | H | Ethoxycarbonyl | Butoxy | Butoxy | reddish-tinged blue |
| 28 | H | tert.-Butyl | 2-Methoxyethoxy | 2-Methoxyethoxy | reddish-tinged blue |
| 29 | H | Methoxy | $(OC_2H_4)_2OCH_3$ | $(OC_2H_4)_2OCH_3$ | red-violet |
| 30 | Methoxy | Chlorine | Methylamino | Methoxy | blue |
| 31 | Carboxyl | Ethyl | Dimethylamino | Ethoxy | blue |
| 32 | Methoxycarbonyl | Benzyl | Diethylamino | Diethylamino | deep blue |
| 33 | Cyano | Cyclohexyl | Morpholino | Morpholino | greenish-tinged blue |
| 34 | H | Ethylsulphonyl | Anilino | Anilino | blue |
| 35 | H | Carboxyl | Chlorine | Methoxy | blue |
| 36 | H | Methyl | Benzyloxy | Benzyloxy | blue |
| 37 | Cyano | H | Piperidino | Butoxyethoxy | reddish-tinged blue |
| 38 | H | Cyano | Diethylamino | Chlorine | reddish-tinged blue |
| 39 | H | Anilinocarbonyl | isopropoxy | isopropoxy | reddish-tinged blue |

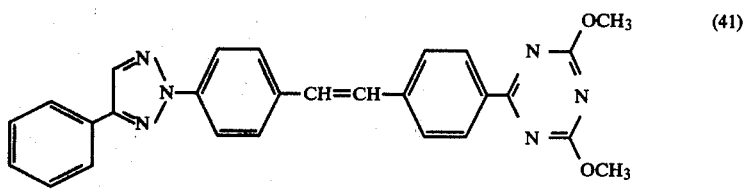 (41)

in 70% yield in the form of greenish-tinged yellow crystals which, after recrystallising from dimethylformamide and xylene, when dissolved in dimethylformamide, give a solution which exhibits intense blue fluorescence.

The stilbene derivatives of the general formula

EXAMPLE 11

Analogously to Example 6, 2,4-di-n-butoxy-6-(4-formylphenyl)-1,3,5-triazine and 5-methoxy-2-(4-dimethoxyphosphonomethyl-phenyl)-2H-benzotriazole give the compound of the formula

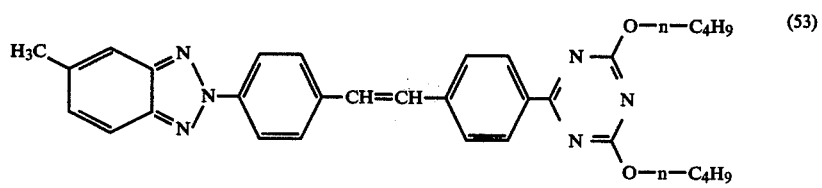 (53)

in the form of pale yellow crystals which exhibit reddish-tinged blue fluorescence in dimethylformamide.

The 2H-benzotriazole derivatives of the general formula

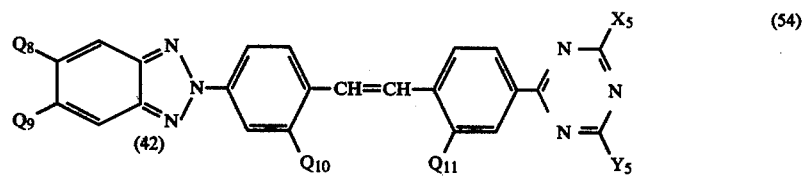 (54)

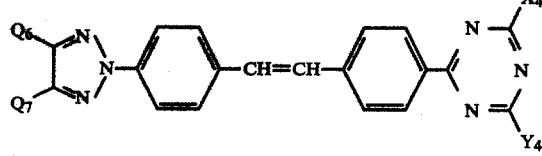 (42)

listed in Table IV are obtained likewise.

listed in Table III can be prepared in the same way.

Table III

| Formula No. | $Q_6$ | $Q_7$ | $X_4$ | $Y_4$ | Colour of fluorescence in dimethylformamide |
|---|---|---|---|---|---|
| 43 | H | Methyl | Butoxy | Butoxy | greenish-tinged blue |
| 44 | Methyl | Methyl | Chlorine | Dimethylamino | greenish-tinged blue |
| 45 | Methyl | Ethyl | Dipropylamino | Dipropylamino | greenish-tinged blue |
| 46 | Phenyl | Methyl | Morpholino | Methoxy | greenish-tinged blue |
| 47 | Phenyl | Phenyl | Piperidino | Ethoxy | greenish-tinged blue |
| 48 | Styryl | Hydrogen | $(OC_2H_4)_2OCH_3$ | $(OC_2H_4)_2OCH_3$ | blue |
| 49 | Phenyl | H | Anilino | Anilino | blue |
| 50 | Chlorine | Phenyl | Ethylamino | Ethylamino | blue |
| 51 | Ethoxycarbonyl | Phenyl | Propoxy | Methoxy | blue |
| 52 | Cyano | Phenyl | 2-Hydroxyethylamino | Butoxy | blue |

Table IV

| Formula No. | $Q_8$ | $Q_9$ | $Q_{10}$ | $Q_{11}$ | $X_5$ | $Y_5$ | Colour of fluorescence in dimethylformamide |
|---|---|---|---|---|---|---|---|
| 55 | Methyl | H | H | H | Diethylamino | Chlorine | blue |
| 56 | Methoxy | H | H | Methoxy | 2-Methoxyethoxy | 2-Methoxyethoxy | reddish-tinged blue |
| 57 | Butoxy | H | H | Cyano | Methylamino | Methylamino | reddish-tinged blue |
| 58 | Methoxy | Chlorine | H | Acetyl | Ethoxy | Ethoxy | reddish-tinged blue |
| 59 | tert.-Butyl | H | H | H | Diethylamino | Diethylamino | blue |
| 60 | Methyl | Methoxy | Cyano | H | Piperidino | 2-Hydroxyethoxy | blue |

The compound of the formula

Table IV-continued

| Formula No. | Q8 | Q9 | Q10 | Q11 | X5 | Y5 | Colour of fluorescence in dimethylformamide |
| --- | --- | --- | --- | --- | --- | --- | --- |

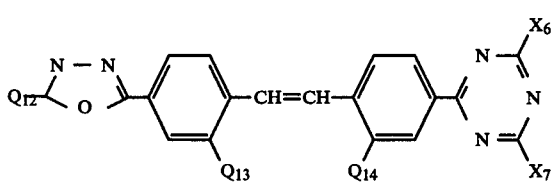
(61)

Colour of fluorescence in dimethylformamide: blue
is prepared in an anlogous manner.

EXAMPLE 12

The oxadiazole derivatives of the general formula (62)

listed in Table V which follows are prepared according to Example 2.

After rinsing and drying, the woven fabric thus treated exhibits a very good whitening effect which is fast to light and which is substantially more brilliant than that which is achieved by treatment with sodium chlorite by itself.

EXAMPLE 15

In a rotary autoclave, a woven fabric consisting of polyester fibres (polyethylene glycol terephthalate) is introduced, in a liquor ratio of 1:40, into a bath which contains, per liter, 1.5 g of sodium oleylsulphonate, 1 g of oxalic acid and 0.05 g of one of the compounds listed under 27 to 3 and 35 to 38 in Table II.

The rotary autoclave is kept at 125° C. for 45 minutes, under moderate agitation. After cooling, the woven fabric is rinsed and dried; it exhibits a clear and attrac- Table V

| Formula No. | Q12 | Q13 | Q14 | X6 | X7 | Colour of fluorescence in dimethylformamide |
| --- | --- | --- | --- | --- | --- | --- |
| 63 | Phenyl | H | H | Methoxy | Methoxy | blue |
| 64 | p-Chlorophenyl | H | Cyano | Isopropoxy | Isopropoxy | reddish-tinged blue |
| 65 | p-Methoxyphenyl | H | H | Butylamino | Ethoxy | deep blue |
| 66 | p-Ethoxycarbonylphenyl | H | Methoxy | 2-Methoxyethoxy | 2-Methoxyethoxy | reddish-tinged blue |
| 67 | p-Biphenyllyl | Cyano | H | Piperidino | Benzyloxy | blue |
| 68 | Styryl | H | Ethoxycarbonyl | (OC2H4)2OCH3 | (OC2H4)2OCH3 | reddish-tinged blue |
| 69 | p-Butoxycarbonylphenyl | H | H | Dipropylamino | Dipropylamino | blue |

EXAMPLE 13

100 g of polyester granules of terephthalic acid and ethylene glycol are intimately mixed with 0.05 g of one of the compounds of the formula (1), (3), (8) or (11) and the mixture is melted at 285° C. whilst stirring. Spinning through customary spinnerets gives strongly brightened polyester fibres.

The compounds of the formula (1), (4), (8) or (11) can also be added to the starting materials before or during the polycondensation.

EXAMPLE 14

A woven fabric consisting of polyethylene glycol terephthalate filaments is treated, in the ratio 1:20, in an aqueous liquor which contains 1 g/l of sodium chloride and, in the dispersed form, 0.05 g/l of one of the brightening agents listed under No. 5, 7 and 10 to 14 in Table I. The bath is brought to 125° C. in 45 minutes in a high temperature (HT apparatus) and the textile material is treated at this temperature for a further 45 minutes.

tive brightening with good fastness to light, washing and chlorite.

EXAMPLE 16

100 parts of polystyrene and 0.1 part of one of the compounds No. 18, 19, 20, 23, 39, 41, 43, 52 or 53 are melted for 20 minutes at 210° C. in a tube having a diameter of 1 cm, with the exclusion of air. Cooling gives an optically brightened polystyrene composition of good fastness to light.

EXAMPLE 17

100 g of polypropylene "Fibre Grade" are intimately mixed with 0.8 of one of the compounds No. 18, 23, 52, 56, 57 or 65 to 69 and the mixture is melted at 280° to 290° C., whilst stirring. The melt is spun and drawn through customary spinnerets by melt spinning processes which are in themselves known. This gives intensely brightened polypropylene fibres.

We claim:
1. Fluorescent dyestuff of the formula

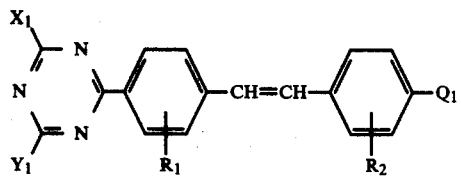

wherein
$X_1$ and $Y_1$ are

—(OCH$_2$—CH$_2$)$_r$—OR$_3$;

$R_1$ and $R_2$ are hydrogen, chlorine, $C_1$-$C_4$-alkyl, $C_1$-$C_4$-alkoxy, $C_1$-$C_4$-alkoxycarbonyl or cyano;
$R_3$ is hydrogen, $C_1$-$C_4$-alkyl, benzyl or phenyl;
$Q_1$ is chlorine, bromine, cyano, carboxyl, $C_1$-$C_4$-alkoxycarbonyl

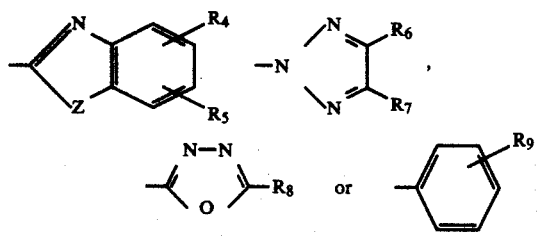

$R_4$ is hydrogen, chlorine, $C_1$-$C_4$-alkyl, phenyl-$C_1$-$C_3$-alkyl, cyclohexyl, phenyl, $C_1$-$C_4$-alkoxy, $C_1$-$C_4$-alkylsulphonyl, $C_1$-$C_4$-alkoxycarbonyl, cyano or carboxyl, or $R_4$ together with $R_5$ forms a fused 1-cyclopentene, 1-cyclohexene or benzene ring or one of the foregoing rings substituted by 1 to 4 methyl groups;
$R_5$ is hydrogen, chlorine or methyl, or $R_5$ together with $R_4$ forms a fused 1-cyclopentene, 1-cyclohexene or benzene ring or one of the foregoing rings substituted by 1 to 4 methyl groups;
$R_6$ is $C_1$-$C_4$-alkyl, phenyl or styrene, or $R_6$ together with $R_7$ forms a fused benzene ring, a fused benzene ring substituted by $C_1$-$C_4$-alkyl, $C_1$-$C_4$-alkoxy or chlorine, or a fused naphthalene ring;
$R_7$ is hydrogen, $C_1$-$C_4$-alkyl or phenyl, or $R_7$ together with $R_6$ forms a fused benzene ring, a fused benzene ring substituted by $C_1$-$C_4$-alkyl, $C_1$-$C_4$-alkoxy or chlorine, or a fused naphthalene ring;
$R_8$ is phenyl, styryl, biphenylyl or naphthyl or one of the foregoing substituted by $C_1$-$C_4$-alkyl, $C_1$-$C_4$-alkoxy, $C_1$-$C_4$-alkoxycarbonyl, cyano or chlorine;
$R_9$ is hydrogen, $C_1$-$C_4$-alkyl, $C_1$-$C_4$-alkoxy, $C_1$-$C_4$-alkoxycarbonyl, cyano, a benzoxazol-2-yl radical, or a benzoxazol-2-yl substituted by $C_1$-$C_4$-alkoxycarbonyl, cyano or chlorine;
Z is O, S or NR$_{10}$
$R_{10}$ is hydrogen, $C_1$-$C_4$-alkyl, acetyl, benzoyl, benzyl or phenyl; and
r denotes an integer from 0 to 2.

2. The fluorescent dyestuff of claim 1, $X_1$ and $Y_1$ are —(OCH$_2$—CH$_2$)$_r$—OR$_{11}$; $Q_1$ is

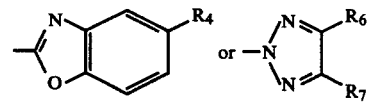

$R_1$ and $R_2$ are hydrogen or cyano;
$R_4$ is hydrogen, chlorine, $C_1$-$C_4$-alkyl, phenyl-$C_1$-$C_3$-alkyl, cyclohexyl, phenyl, $C_1$-$C_4$-alkoxy, $C_1$-$C_4$-alkylsulphonyl, $C_1$-$C_4$-alkoxycarbonyl, cyano or carboxyl;
r is an integer from 0 to 2; and
$R_{11}$ is $C_1$-$C_4$-alkyl.

3. The fluorescent dyestuff of claim 1, having the formula

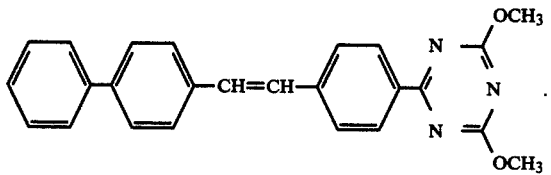

4. The fluorescent dyestuff of claim 1, having the formula

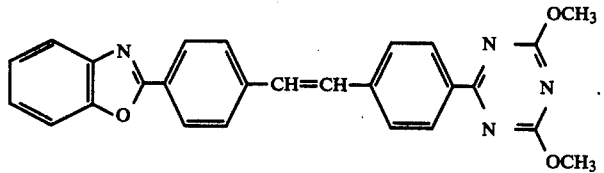

5. Synthetic, semi-synthetic or natural organic high-molecular material whitened with the fluorescent dyestuff of claim 1.

6. A process for whitening synthetic, semi-synthetic or natural organic high-molecular weight material comprising applying to said material or incorporating in said material a fluorescent dyestuff of claim 1.

* * * * *